US012605134B2

(12) United States Patent
Miyake et al.

(10) Patent No.: US 12,605,134 B2
(45) Date of Patent: Apr. 21, 2026

(54) IMAGING CONTROL APPARATUS AND RADIATION IMAGING SYSTEM

(71) Applicant: Konica Minolta, Inc., Tokyo (JP)

(72) Inventors: Nobuyuki Miyake, Kanagawa (JP); Kosuke Fukazu, Tokyo (JP); Keisuke Koeda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 276 days.

(21) Appl. No.: 18/310,140

(22) Filed: May 1, 2023

(65) Prior Publication Data

US 2023/0263496 A1 Aug. 24, 2023

Related U.S. Application Data

(63) Continuation of application No. 17/173,630, filed on Feb. 11, 2021, now Pat. No. 11,672,502.

(30) Foreign Application Priority Data

Feb. 19, 2020 (JP) ................................. 2020-026304

(51) Int. Cl.
*A61B 6/00* (2024.01)
*H04N 23/30* (2023.01)
(52) U.S. Cl.
CPC ............ *A61B 6/542* (2013.01); *A61B 6/5205* (2013.01); *A61B 6/5294* (2013.01); *H04N 23/30* (2023.01)
(58) Field of Classification Search
CPC ..... A61B 6/5205; A61B 6/5294; A61B 6/542; H04N 5/32
See application file for complete search history.

(56) References Cited

U.S. PATENT DOCUMENTS

| | | | |
|---|---|---|---|
| 2009/0016484 A1 | 1/2009 | Wang | |
| 2009/0022273 A1* | 1/2009 | Kashiwagi | A61B 6/542 |
| | | | 378/37 |
| 2012/0163687 A1 | 6/2012 | Plakas | |
| 2013/0121464 A1 | 5/2013 | Tajima | |
| 2013/0148782 A1 | 6/2013 | Tajima | |

(Continued)

FOREIGN PATENT DOCUMENTS

| | | |
|---|---|---|
| JP | 2008-178674 A | 8/2008 |
| JP | 2009-297284 A | 12/2009 |

(Continued)

OTHER PUBLICATIONS

Notice of Reasons for Rejection dated Aug. 29, 2023 for corresponding Japanese Patent Application No. 2020-026304, together with English translation.

(Continued)

*Primary Examiner* — Blake C Riddick
(74) *Attorney, Agent, or Firm* — LUCAS & MERCANTI, LLP

(57) ABSTRACT

An imaging control apparatus includes a hardware processor that acquires a first imaging condition set as a imaging condition for a preliminary exposure performed prior to a main exposure that performs an exposure of radiation on a subject, and the hardware processor performs control based on compatibility of the acquired first imaging condition and a second imaging condition input as an imaging condition for the subject.

15 Claims, 7 Drawing Sheets

<u>100</u>

(56) References Cited

U.S. PATENT DOCUMENTS

| | | | |
|---|---|---|---|
| 2014/0185764 | A1 | 7/2014 | Takenaka |
| 2014/0205066 | A1 | 7/2014 | Kitagawa |
| 2015/0055753 | A1 | 2/2015 | Tajima |
| 2015/0189194 | A1 | 7/2015 | Tajima |
| 2015/0297165 | A1 | 10/2015 | Tanaka |
| 2015/0363926 | A1 | 12/2015 | Enomoto |
| 2016/0220216 | A1 | 8/2016 | Karahashi |
| 2017/0143292 | A1 | 5/2017 | Yun |
| 2018/0000442 | A1 | 1/2018 | Hiroike |
| 2018/0031714 | A1 | 2/2018 | Tajima |
| 2018/0199907 | A1 | 7/2018 | Hatakeyama |
| 2019/0365338 | A1 | 12/2019 | Haider |
| 2020/0187876 | A1 | 6/2020 | Imamura |
| 2021/0383514 | A1 | 12/2021 | Kitano |

FOREIGN PATENT DOCUMENTS

| | | | |
|---|---|---|---|
| JP | 2013-138828 | A | 7/2013 |
| JP | 2014-200306 | A | 10/2014 |
| JP | 2019-126709 | A | 8/2019 |

OTHER PUBLICATIONS

Japanese Patent Office, Notice of Reasons for Refusal mailed Jan. 30, 2024 for corresponding Japanese Patent Application No. 2020-026304, together with English translation, 6 pages.

* cited by examiner

100

2

3

| No | Imaging area | Imaging direction | Tube voltage range | Upper limit of tube current time product |
|----|----|----|----|----|
| 1 | Chest | Front | Less than 100 kv | 30mAs |
| 2 | | | 100 kv or more | 10mAs |
| 3 | Chest | Side | Less than 100 kv | 90mAs |
| 4 | | | 100 kv or more | 30mAs |
| . . . | . . . | . . . | . . . | . . . |

34

| No | Imaging area | Imaging direction | Tube voltage | Upper limit of tube current time product |
|---|---|---|---|---|
| 1 | Chest | Front | 50kV | 60mAs |
| 2 | | | 80kV | 30mAs |
| 3 | | | 120kV | 10mAs |
| 4 | Chest | Side | 50kV | 180mAs |
| 5 | | | 80kV | 90mAs |
| 6 | | | 120kV | 30mAs |
| . . . | . . . | . . . | . . . | . . . |

FIG. 9

| No | Imaging area | Imaging direction | Tube voltage range | Upper limit of tube current time product | Lower limit of tube current time product |
|---|---|---|---|---|---|
| 1 | Chest | Front | Less than 100 kV | 30mAs | 0.3mAs |
| 2 | | | 100 kV or more | 10mAs | 0.1mAs |
| 3 | Chest | Side | Less than 100 kV | 90mAs | 0.9mAs |
| 4 | | | 100 kV or more | 30mAs | 0.3mAs |
| . . . | . . . | . . . | . . . | . . . | . . . |

FIG. 10

| No | Type of radiation irradiation apparatus | Lower limit of irradiation time |
|----|----|----|
| 1 | Apparatus A | 4msec |
| 2 | Apparatus B | 2msec |
| .<br>.<br>. | .<br>.<br>. | .<br>.<br>. |

FIG. 11

| No | Imaging area | Imaging direction | Distance from irradiation surface center of imaging table to upper boundary of irradiation field | Distance from irradiation surface center of imaging table to lower boundary of irradiation field | Distance from irradiation surface center of imaging table to left boundary of irradiation field | Distance from irradiation surface center of imaging table to right boundary of irradiation field |
|----|----|----|----|----|----|----|
| 1 | Chest | Front | 20cm | 19cm | 18cm | 18cm |
| 2 | Chest | Side | 20cm | 19cm | 16cm | 16cm |
| 3 | Hand | Front | 14cm | 14cm | 14cm | 14cm |
| .<br>.<br>. | .<br>.<br>. | .<br>.<br>. | .<br>.<br>. | .<br>.<br>. | .<br>.<br>. | .<br>.<br>. |

FIG. 12

IMAGING CONTROL APPARATUS AND RADIATION IMAGING SYSTEM

CROSS REFERENCE TO RELATED APPLICATIONS

This application is a Continuation of U.S. application Ser. No. 17/173,630 filed Feb. 11, 2021, which claimed the priority of Japanese Patent Application No. 2020-026304, filed on Feb. 19, 2020, both of which are incorporated herein by reference in its entirety.

BACKGROUND

Technological Field

The present invention relates to an imaging control apparatus and a radiation imaging system.

Description of Related Art

Commonly known radiation imaging systems include an automatic exposure control function that performs a main exposure and a preliminary exposure prior to the main exposure when taking radiation images. In the automatic exposure control function, the preliminary exposure is performed at a dose lower than that of the main exposure, and the imaging conditions such as the dose for the main exposure are decided based on the obtained image in the preliminary exposure (hereinafter also referred to as "preliminary exposure image") and the incidental information associated with the preliminary exposure image (for example, the irradiation time in the preliminary exposure).

Japanese Patent Application Laid-Open No. 2019-126709, for example, discloses a configuration for determining whether or not a preliminary exposure image could have been appropriately captured from an image analysis of the preliminary exposure image. When the result of the image analysis is appropriate, image capturing in the main exposure is continued, and when the result of the image analysis is not appropriate, image capturing in the main exposure is stopped.

Further, Japanese Patent Application Laid-Open No. 2008-178674 discloses a configuration for determining whether or not a dose per unit time is equal to or higher than a specified value in a exposure by automatic exposure control, and reporting an alert when the dose is equal to or higher than the specified value.

SUMMARY

For obtaining an exposure dose from a preliminary exposure image, however, image capturing in a preliminary exposure under an inappropriate imaging condition may cause failure in taking an appropriate preliminary exposure image, and consequently, it may become impossible to appropriately take images in the main exposure.

The configuration described in Japanese Patent Application Laid-Open No. 2019-126709 determines whether or not the preliminary exposure image was properly taken after the image capturing, thus the preliminary exposure performed may be wasted. The configuration may need further improvement for appropriately taking images in the main exposure.

When the configuration described in Japanese Patent Application Laid-Open No. 2008-178674 is applied to the automatic exposure control performing a preliminary exposure and a main exposure, it is not possible to properly understand the cumulative dose of imaging obtained in the preliminary exposure by the determination based solely on the dose per unit time. For example, even with a large dose per unit time, short irradiation time may reduce the cumulative dose, and then the dose may become suitable for the preliminary exposure. Therefore, the imaging conditions obtained from the preliminary exposure cannot be detected as appropriate.

An object of the present invention is to provide an imaging control apparatus and a radiation imaging system capable of performing preliminary exposure under appropriate imaging conditions.

To achieve at least one of the abovementioned objects, an imaging control apparatus reflecting one aspect of the present invention includes:

a hardware processor that acquires a first imaging condition set as a imaging condition for a preliminary exposure performed prior to a main exposure that performs an exposure of radiation on a subject, in which the hardware processor performs control based on compatibility of the acquired first imaging condition and a second imaging condition input as an imaging condition for the subject.

To achieve at least one of the abovementioned objects, a radiation imaging system reflecting one aspect of the present invention includes:

a radiation irradiation apparatus that emits radiation for exposure;

a radiation imaging apparatus that generates image data of an exposure image by receiving the radiation exposure; and the above imaging control apparatus.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 9 illustrates an exemplary table in which a plurality of first imaging conditions are described;

FIG. 10 illustrates an exemplary table in which a plurality of first imaging conditions are described;

FIG. 11 illustrates an exemplary table in which a plurality of first imaging conditions are described;

FIG. 12 illustrates an exemplary table in which a plurality of first imaging conditions are described;

DETAILED DESCRIPTION OF EMBODIMENTS

Hereinafter, one or more embodiments of the present invention will be described with reference to the drawings. However, the scope of the invention is not limited to the disclosed embodiments.

Figure 1:
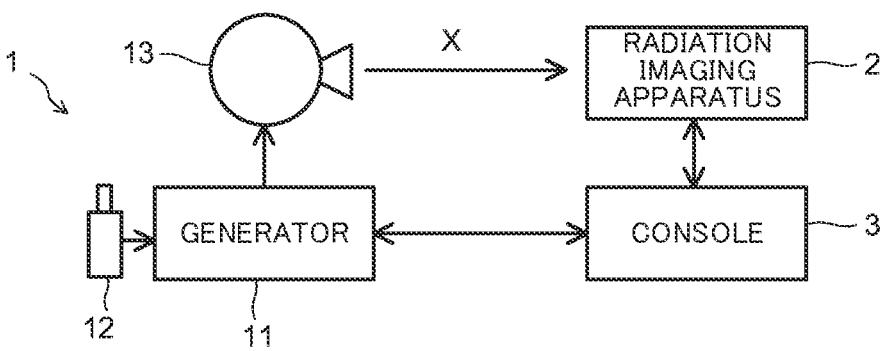
FIG. 1 is a block diagram illustrating a configuration of a radiation imaging system according to an embodiment of the present invention.

Hereinafter, an embodiment of the present invention will be described in detail with reference to the accompanying drawings. FIG. 1 is a block diagram illustrating a configuration of radiation imaging system 100 according to an embodiment of the present invention.

As shown in FIG. 1, radiation imaging system 100 according to the present embodiment is configured to include radiation irradiation apparatus 1, radiation imaging apparatus 2 and console 3. Further, radiation imaging system 100 is connectable to Radiology Information System (RIS) and Picture Archiving and Communication System (PACS) and/or the like (not shown).

Radiation irradiation apparatus 1 is connected to console 3 so as to be able to communicate thereto by wire or wirelessly. Further, radiation irradiation apparatus 1 is configured to include generator 11, exposure switch 12 and radiation source 13.

Generator 11 is capable of applying a voltage in accordance with preset radiation exposure conditions (for example, tube voltage, tube current, irradiation time, product of tube current and time (mAs-value)—hereinafter also referred to as "tube current time product")—to radiation source 13, based on the operation of exposure switch 12.

Radiation source 13 (tube bulb) includes a rotating anode and a filament and the like (not shown). When generator 11 applies a voltage, the filament irradiates the rotating anode with an electron beam corresponding to the applied voltage, and the rotating anode then generates radiation X (for example, X-ray) with a dose corresponding to the intensity of the electron beam.

FIG. 1 illustrates an example including separated generator 11, exposure switch 12 and radiation source 13, but the components may be integrally configured. FIG. 1 illustrates an example including exposure switch 12 connected to generator 11, but exposure switch 12 may be provided in another apparatus. Radiation irradiation apparatus 1 may be installed in an imaging room, or may be configured to be movable by being incorporated in a round-trip vehicle for examination or the like.

Radiation imaging apparatus 2 is connected to console 3 so as to be able to communicate thereto by wire or wirelessly. Radiation imaging apparatus 2 is configured such that it can generate image data of an exposure image of a subject by receiving radiation X exposure through the subject from radiation irradiation apparatus 1.

Figure 2:
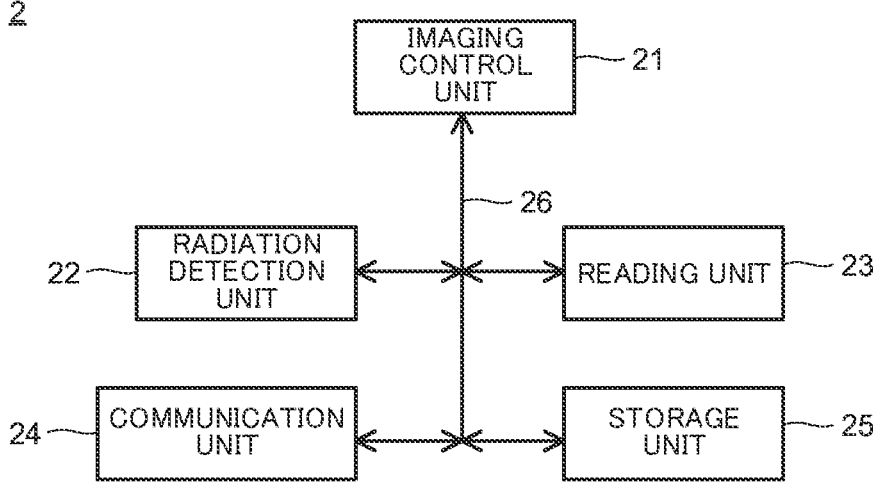
FIG. 2 is a block diagram illustrating a specific configuration of a radiation imaging apparatus.

As shown in FIG. 2, radiation imaging apparatus 2 is configured to include imaging control unit 21, radiation detection unit 22, reading unit 23, communication unit 24, storage unit 25, and bus 26 for connecting the units.

Imaging control unit 21 includes a central processing unit (CPU), a random access memory (RAM), and the like. The CPU of imaging control unit 21 reads various programs stored in storage unit 25, loads the programs in the RAM, executes various processes according to the loaded programs, and centrally controls the behavior of each unit in the radiation imaging apparatus 2 based on a control signal or the like received from an external apparatus such as console 3.

Radiation detection unit 22 includes a substrate in which pixels equipped with a switch element and a radiation detection element generating electric charge according to a dose by receiving radiation X are arranged in a two-dimensional shape (matrix shape).

Reading unit 23 is capable of reading the amount of the electric charge discharged from each pixel as a signal value, and generating image data from a plurality of signal values.

Communication unit 24 is capable of receiving various control signals, various data and the like from an external apparatus, and transmitting various control signals, generated image data and the like to the external apparatus.

Storage unit 25 includes a nonvolatile semiconductor memory, a hard disk and the like, and stores various programs to be executed by imaging control unit 21, parameters necessary for the execution of the programs, and the like. Storage unit 25 is also capable of storing image data generated by reading unit 23 and various data processed by imaging control unit 21.

With imaging control unit 21 turning off the switch elements of radiation detection unit 22, radiation imaging apparatus 2 having the above described configuration accumulates electric charge in each pixel according to the radiation dose upon receiving radiation exposure. When imaging control unit 21 turns on each switch element and the electric charge is discharged from each pixel, reading unit 23 converts each electric charge amount into a signal value and reads it out as image data.

Radiation imaging apparatus 2 may have a configuration such that a scintillator or the like is incorporated, the scintillator converts emitted radiation X into light with another wavelength such as visible light, and electric charge according to the converted light is generated, or a configuration such that the electric charge is directly generated from radiation X without passing through the scintillator or the like. Radiation imaging apparatus 2 may be a dedicated machine type integrated with an imaging table, or a portable type.

Console 3 includes a PC, a portable terminal or a dedicated apparatus, and is connected to, for example, radiation irradiation apparatus 1 and radiation imaging apparatus 2 so as to be able to communicate thereto by wire or wirelessly. Console 3 can set the imaging conditions of radiation irradiation apparatus 1 and radiation imaging apparatus 2, the imaging target area, and the like based on the imaging order from an external apparatus (RIS or the like) or the operation from a user. Console 3 corresponds to "imaging control apparatus" of the present invention.

Figures 3, 4:
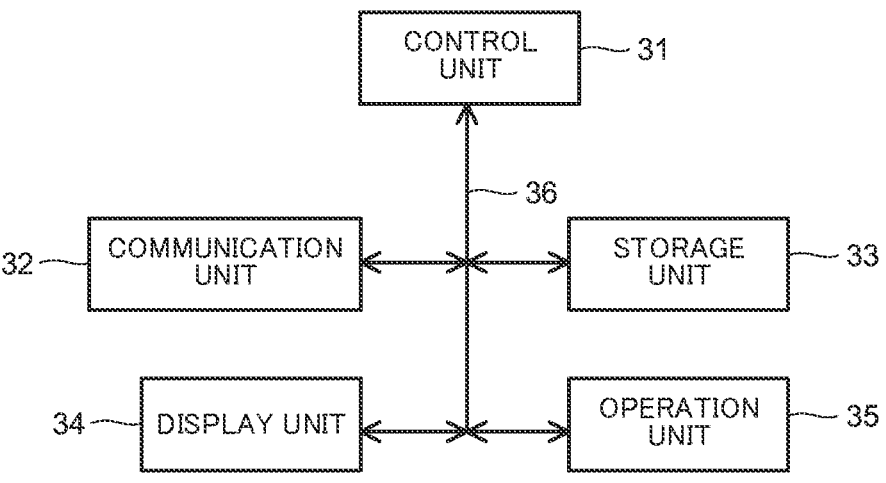
FIG. 3 is a block diagram illustrating a specific configuration of a console.
FIG. 4 illustrates an exemplary table in which a plurality of first imaging conditions are described.

As shown in FIG. 3, console 3 is configured to include control unit 31, communication unit 32, storage unit 33, display unit 34, operation unit 35 and bus 36 for connecting the units.

Control unit 31 includes a CPU, a RAM and the like. The CPU of control unit 31 reads various programs stored in storage unit 33 according to the operation from operation unit 35, loads the programs in the RAM, executes various processes according to the loaded programs, and centrally controls the behavior of each unit of console 3.

Communication unit 32 includes a LAN adapter, a modem, a terminal adapter (TA) and the like, and controls data transmission and reception with each apparatus connected to a communication network.

Storage unit 33 includes a nonvolatile semiconductor memory, a hard disk and the like, and stores various programs to be executed by control unit 31, parameters necessary for the execution of the programs, and the like. Further, storage unit 33 can store the image data received from radiation imaging apparatus 2 and the image data processed by control unit 31 so that the image date associates with the incidental information.

Display unit 34 includes a monitor such as a liquid crystal display (LCD) or a cathode ray tube (CRT), and displays input instruction, data and the like from operation unit 35 according to the instruction of a display signal input from control unit 31.

Operation unit 35 is configured to include a keyboard provided with cursor keys, numeric input keys, various function keys and the like, and a pointing apparatus such as a mouse. Operation unit 35 outputs an instruction signal input by a key operation via the keyboard or a mouse operation to control unit 31. Operation unit 35 may be provided with a touch panel on the display screen of display unit 34, and, in this case, operation unit 35 outputs an instruction signal input through the touch panel to control unit 31.

In the following, the imaging control of radiation imaging apparatus 2 by control unit 31 will be described. Control unit 31 performs an automatic exposure control to decide the imaging conditions for a main exposure based on a preliminary exposure image obtained in a preliminary exposure and the incidental information associated with the preliminary exposure image. The preliminary exposure is performed prior to the main exposure at a dose lower than that of the main exposure.

Control unit 31 acquires a first imaging condition in the preliminary exposure based on the examination condition of a subject and a second imaging condition from the user. Control unit 31 corresponds to "acquiring unit" of the present invention.

Examples of the examination condition of the subject includes conditions such as the imaging areas of the subject (e.g., chest, abdomen and lumbar spine) and imaging directions (e.g., front, back, side and oblique). Examples of the second imaging condition from the user include conditions relating to a tube voltage (kV) used for the preliminary exposure, and a cumulative dose such as a tube current time product (mAs). The tube current time product may also be a combination of a tube current and an irradiation time. Examples of the imaging condition, such as the first imaging condition, in the preliminary exposure include conditions relating to a tube voltage (kV) used for the preliminary exposure, and a cumulative dose range such as a tube current time product (mAs) or the like. The tube current time product may also be a combination of a tube current and an irradiation time.

The first imaging condition in the preliminary exposure is an imaging condition that enables appropriate imaging in the preliminary exposure, and is set for each examination condition of a subject. Storage unit 33 stores a table in which the plurality of first imaging conditions linked with each examination condition of the subject are described. For example, FIG. 4 illustrates an exemplary table in which ranges of tube voltages and the upper limits of tube current time products linked with the imaging areas and imaging directions are described.

Control unit 31 refers to the table of storage unit 33 to select a first imaging condition corresponding to the examination condition of a subject from the plurality of first imaging conditions. For example, when the user inputs conditions—chest, front, a tube voltage of 120 kV, and a tube current time product of 15 mAs, control unit 31 acquires the first imaging condition of No. 2 having the conditions—chest, front, and a tube voltage in a range of 100 kV or more—from the table shown in FIG. 4.

Control unit 31 then performs control based on the compatibility of the second imaging condition input as an imaging condition of the subject and the acquired first imaging condition. In other words, control unit 31 performs the control to assist the user so that the second imaging condition input from the user for the subject falls within the range of the first imaging condition (hereinafter also referred to as "first imaging condition range"). Specifically, control unit 31 compares the first imaging condition to the second imaging condition to determine whether or not the second imaging condition falls within the first imaging condition range.

In the above cases, while the tube current time product input by the user is 15 mAs, the upper limit of the tube current time product in the first imaging condition of No. 2 is 10 mAs. Control unit 31 thus determines that the second imaging condition falls out of the first imaging condition range.

When the second imaging condition does not fall within the first imaging condition range, control unit 31 prohibits the exposure by radiation imaging apparatus 2 and the generation of an exposure image in the exposure, and further outputs a warning command to the user. The warning command may be, for example, a command which relates to the behavior of a device and acts on the user's vision, such as a display on display unit 34, or a command which relates to the behavior of a device and acts on the user's tactile sense, such as vibration given by operation unit 35.

This configuration allows the user to notice that the second imaging condition does not fall within the first imaging condition range. As a result, the configuration can guide the user so that the second imaging condition from the user falls within the first imaging condition range in a preliminary exposure, and thus the preliminary exposure can be performed under the optimal conditions.

Examples of the command which relates to the behavior of a device and acts on the user's vision include a behavior command that changes the color of the light of a hand switch used to operate the device by the user to a color dedicated to the warning. Examples of the command which relates to the behavior of the device and acts on the user's tactile sense include a command that causes the vibration at a warning by providing a vibration function in the hand switch, or a behavior command that changes the vibration pattern of the vibration. When a user presses the hand switch, the user often watches whether the subject is in the proper condition for the image capturing. Notifying the user with the hand switch in the user's hand allows the user to know the presence of the notification with smaller line-of-sight movement than notifying the user only by display unit 34 does, thereby increasing the workability. Both display unit 34 and the hand switch may notify the user. For example, the hand switch may notify the user of simple information that indicates the second imaging condition is not within the range, and display unit 34 may notify the user of more detailed information than that of the hand switch as described below. Such a configuration can achieve both a small line-of-sight movement of the user and an accurate understanding of the cause of the abnormality and the action to be taken, thereby further increasing workability.

Other than the warning command, control unit 31 may notify the user of the determination result whether or not the second imaging condition is within the first imaging condition range with, for example, a command for displaying that the second imaging condition is outside the first imaging condition range by characters or the like, or a command to convey that it is out of the first imaging condition range by voice.

Figure 5:
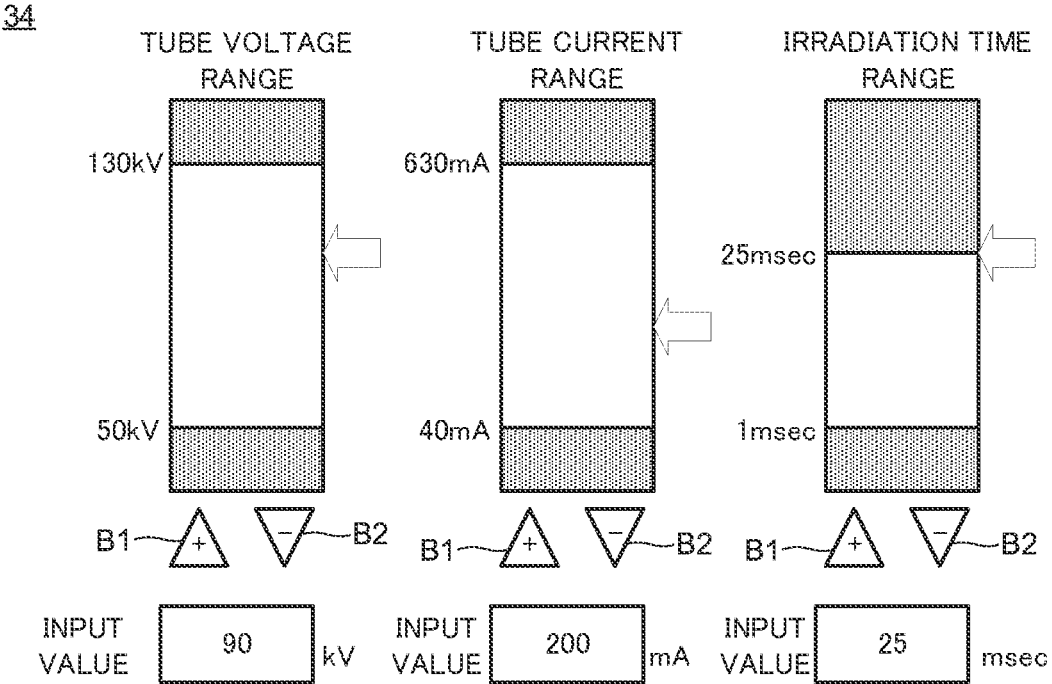
FIG. 5 illustrates an exemplary representation for the range of the first imaging condition.

Control unit 31 may also notify the user of the acquired first imaging condition range. Specifically, control unit 31 may display the first imaging condition range on display unit 34. For example, FIG. 5 shows an example in which the ranges of the tube voltage, the tube current, and the irradiation time are displayed on display unit 34.

In this example, the position of an arrow indicates the input value of the second imaging condition, dots show the outside of the first imaging condition range. In addition, button B1 for increasing the input value and button B2 for decreasing the input value are displayed in this example.

This configuration allows the user to easily determine whether the input value of the second imaging condition is within the first imaging condition range.

In addition, buttons B1 and B2 for increasing or decreasing the input value may also include a display that allows the user to determine whether or not the second imaging condition falls within the first imaging condition range after the pressing of the button B1 or B2.

Figure 6:
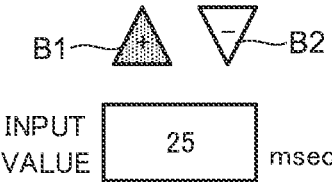
FIG. 6 illustrates an exemplary display for the button shown in FIG. 5.

For example, if more pressing of the button causes the second imaging condition to fall out of the first imaging condition range, dots may be displayed on the button. FIG. 6 shows a display example in which the user can determine that the second imaging condition would be out of the first imaging condition range when button B1 for the input value of the irradiation time is pressed to increase the input value. The example shown in FIG. 6 may be an example in which buttons B1 and B2 according to the example shown in FIG. 6 are applied to the example shown in FIG. 5, or an example in which the range of the tube voltage and the like in FIG. 5 are not displayed.

Alternatively or additionally, when the second imaging condition is out of the first imaging condition range, another display is possible such that the user can determine that pressing the button would allow the second imaging condition to approach the first imaging condition range.

Figure 7:
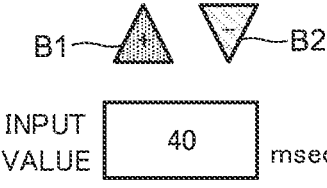
FIG. 7 illustrates an exemplary display for the button shown in FIG. 5.

For example, FIG. 7 shows a display example in which the user can determine that the second imaging condition would approach the first imaging condition range when button B2 for the input value of the irradiation time is pressed to decrease the input value. Button B2 is hatched. The example shown in FIG. 7 may be an example in which buttons B1 and B2 according to the example shown in FIG. 7 are applied to the example shown in FIG. 5, or an example in which the range of the tube voltage and the like in FIG. 5 are not displayed.

Further, the number of button pressing required for the second imaging condition to fall within the first imaging condition range may be displayed. For example, when the second imaging condition would fall within the first imaging condition range by pressing the button three times, the number "3" may be displayed in the vicinity of the button. By indicating the direction in which the second imaging condition would become appropriate or inappropriate in this way, the user can input an appropriate second imaging condition with a small number of operations. This configuration also prevents the user from inputting an inappropriate second imaging condition.

In the case of control in which only the main exposure is performed without performing the preliminary exposure, the imaging condition used in this case is different from the first imaging condition in the preliminary exposure.

Figure 8:
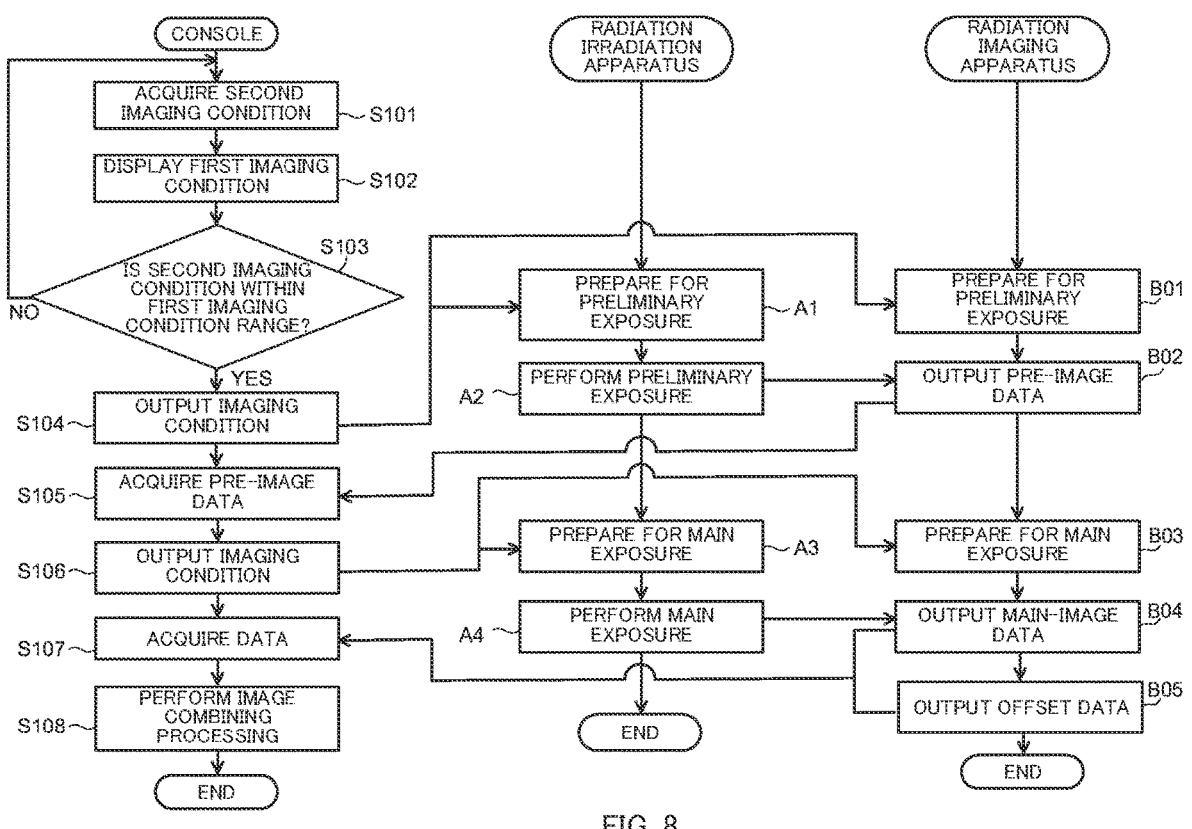
FIG. 8 is a ladder chart showing the behavior of the radiation imaging system during the image capturing.

In the following, the operation of radiation imaging system 100 will be described. FIG. 8 is a ladder chart showing the operation of radiation imaging system 100 during the image capturing.

Console 3 acquires an examination condition of a subject and a second imaging condition (Step S101). Console 3 acquires a first imaging condition from storage unit 33 based on the acquired examination condition and the second imaging condition, and displays the first imaging condition on display unit 34 (Step S102).

Console 3 compares the first imaging condition and the second imaging condition, and determines whether or not the second imaging condition is within the first imaging condition range (Step S103). When the second imaging condition is not within the first imaging condition range as a result of the determination (Step S103, NO), the process returns to Step S101. At this time, console 3 may output a warning to the user.

On the other hand, when the second imaging condition is within the first imaging condition range (Step S103, YES), console 3 outputs the imaging condition of the preliminary exposure to radiation irradiation apparatus 1 and radiation imaging apparatus 2 (Step S104).

When the imaging condition of the preliminary exposure is input, radiation irradiation apparatus 1 compares the imaging condition of the preliminary exposure with the range of a fifth imaging condition in radiation irradiation apparatus 1. When the imaging condition of the preliminary exposure is within the range of the fifth imaging condition, radiation irradiation apparatus 1 sets the imaging condition for the preliminary exposure, and prepares for the preliminary exposure (Step A1). The fifth imaging condition is generally defined by narrower ranges between the ranges of the tube voltage, the tube current and the tube current time product corresponding to generator 11 of radiation irradiation apparatus 1, and the ranges of the tube voltage, the tube current and the tube current time product corresponding to radiation source 13. For example, when the tube voltage of generator 11 corresponds to a range from 50 kV to 150 kV, and the tube voltage of radiation source 13 corresponds to a range from 40 kV to 125 kV, the tube voltage of the fifth imaging condition becomes in a range from 50 kV to 125 kV. These ranges are restrictions due to the performance of radiation irradiation apparatus 1, and since a common range is used for both preliminary exposure and main exposure, whether the imaging condition is appropriate for preliminary exposure cannot be determined. When the imaging condition for preliminary exposure is input, radiation imaging apparatus 2 sets the imaging condition for the preliminary exposure and prepares for the preliminary exposure (Step B01).

Subsequently, when the user presses exposure switch 12, radiation irradiation apparatus 1 emits radiation for exposure toward the subject and radiation imaging apparatus 2 based on the imaging condition of the preliminary exposure (Step A2).

When radiation imaging apparatus 2 receives radiation exposure, radiation imaging apparatus 2 accumulates the electric charge generated based on the radiation dose by each radiation detection element in each pixel, converts the electric charge amounts of each pixel into a signal value, and read the signal value out as pre-image data and output the pre-image data to console 3 (Step B02).

Console 3 acquires the pre-image data (Step S105), calculates the imaging condition of the main exposure by performing an image analysis process or the like on the acquired pre-image data, and outputs the imaging condition to radiation irradiation apparatus 1 and radiation imaging apparatus 2 (Step S106).

When imaging condition of main exposure is input, both of radiation irradiation apparatus 1 and radiation imaging apparatus 2 set the imaging condition for each apparatus and prepare for the main exposure (Steps A3 and B03).

Subsequently, when the user presses exposure switch 12, radiation irradiation apparatus 1 emits radiation for exposure toward the subject and radiation imaging apparatus 2 based on the imaging condition of the main exposure (Step A4).

When radiation imaging apparatus 2 receives radiation exposure, radiation imaging apparatus 2 accumulates the electric charge generated based on the radiation dose by each radiation detection element in each pixel, converts the electric charge amounts of the pixels into signal values, and read the signal values out as main-image data and output the main-image data to console 3 (Step B04).

Further, radiation imaging apparatus 2 accumulates dark electric charge in each pixel, converts the amount of dark electric charge in each pixel into a signal value, reads it out as offset data, and outputs the offset data to console 3 (step B05). The process of Step B05 may be performed before Step B04.

Console 3 acquires the main-image data and the offset data (step S107), performs image combining processing on the main-image data by using the above described pre-image data after performing predetermined image processing (step S108). The image capturing in radiation imaging system 100 is then completed.

Image combining processing is performed on the pre-image data and the main-image data in Step S108, but in a configuration with no image combining processing being performed, the process of step S108 may be omitted. However, from the viewpoint of utilizing the exposure dose in the preliminary exposure for the diagnosis of a patient without wasting the doze, the image combining processing of the pre-image data and the main-image data may preferably be performed.

The present embodiment configured as described above performs the control to assist the user to set the second imaging condition to fall within the first imaging condition range in the preliminary exposure, and thus the preliminary exposure can be performed under the optimal imaging condition.

When the preliminary exposure before the main exposure is performed under inappropriate imaging conditions, radiation imaging system 100 cannot properly capture images.

For example, if the cumulative dose in the preliminary exposure is too large, some pixels will have their pixel values attached to the maximum value. Since it is unclear whether such a pixel value corresponds to the maximum value or is larger than the maximum value, the dose in the preliminary exposure cannot be calculated accurately when this pixel value is used.

Further, if the cumulative dose in the preliminary exposure is too small, the SN ratio of the pixel value deteriorates, so that the dose in the preliminary exposure cannot be calculated accurately when this pixel value is used. For these reasons, it is necessary to set the cumulative dose in the preliminary exposure to an appropriate condition.

If the irradiation time in the preliminary exposure is too short, the radiation output would generally become unstable due to the too short irradiation time, so the dose in the preliminary exposure calculated from the pixel values would also become unstable. As a result, the imaging conditions in the main exposure also become unstable.

If the irradiation time in the preliminary exposure is too long, the body movement of a subject from the start of image capturing to the end of the image capturing is more likely to become large, thus the image capturing that needs to keep the body movement within a certain range may result in failure.

For these reasons, it is necessary to set the irradiation time in the preliminary exposure to an appropriate condition.

An adjusted irradiation field in the preliminary exposure may cause a dose obtained from the preliminary exposure to be inaccurately calculated.

As described above, when the preliminary exposure is performed under inappropriate imaging conditions, radiation imaging system 100 may not be able to perform appropriate image capturing, and the subject may be unnecessarily exposed.

The present embodiment can guide a user to set the second imaging condition to fall within the first imaging condition range by determining whether the second imaging condition is within the first imaging condition. That is, the preliminary exposure can be performed under an appropriate imaging condition, so that images can be appropriately captured in the main exposure in the present embodiment.

In addition, since the first imaging condition range is displayed (notified) to the user, the user can easily notice whether or not the second imaging condition is within the first imaging condition range.

In the above embodiment, the first imaging condition was acquired with reference to the table shown in FIG. 4, but the present invention is not limited thereto. For example, the first imaging condition may be acquired with reference to the table shown in FIG. 9.

In this table, the combination of the tube voltage and the upper limit of the tube current time product is linked with a combination of the imaging area and the imaging direction. Three tube voltages are set for each combination of the imaging area and the imaging direction. In other words, three combinations of the tube voltage and the upper limit of the tube current time product are set for each combination of the imaging area and the imaging direction.

In such a table, the tube current time product can be calculated by linear interpolation. Here is an example having an examination condition in which the imaging area is chest and the imaging direction is front, and a second imaging condition in which the tube voltage is 110 kV and the tube current time product is 12 mAs.

In this example, the tube voltage in the second imaging condition is a value between the tube voltage in No. 2 and the tube voltage in No. 3. Accordingly, control unit 31 refers to the upper limit value (30 mAs) of the tube current time product in No. 2 and the upper limit value (10 mAs) of the tube current time product in No. 3.

Control unit 31 calculates a first ratio of the absolute value of the difference between the tube voltage in No. 2 and the tube voltage in No. 3 (120 kV–80 kV=40 kV) to the absolute value of the difference between the tube voltage in No. 3 and the input tube voltage (120 kV–110 kV=10 kV). The calculated first ratio is 4:1.

Control unit 31 then calculates a second ratio of the absolute value of a first difference between the upper limit value of tube current time product in No. 2 and the upper limit value of tube current time product in No. 3 to the absolute value of a second difference between the upper limit value of tube current time product in 110 kV and the upper limit value of tube current time product in No. 3. The calculated first difference is 30 mAs−10 mAs=20 mAs.

From the second ratio becoming equal to the first ratio, the first difference being 20 mAs and the first ratio being 4:1, the second difference becomes 5 mAs. From the upper limit of tube current time product in No. 3 being 10 mAs, the tube current time product at 110 kV becomes 15 mAs.

Since the tube current time product in the second imaging condition is 12 mAs, it is less than 15 mAs, which is the first imaging condition calculated by the linear interpolation. As a result, control unit 31 determines that the second imaging condition falls in the first imaging condition range. Since there are many combinations of the imaging areas and the imaging directions, the data size becomes very large if a table is provided for each combination; however, when the second imaging condition is calculated from the values of the table in this way, an inexpensive computer can be used because the data size of each table can be compressed, which is economical. Since a range of highly accurate second imaging condition with a smaller data size can be provided, the user has more choices of the first imaging conditions, and the user can capture images under a highly desired first imaging condition as a result.

In the table shown in FIG. 9, an interpolation method other than the linear interpolation may be used.

A combination of a tube voltage range and an upper limit of a tube current time product is used in the table of the above embodiment, but the present invention is not limited thereto. For example, a combination of a tube voltage range, and upper and lower limit values of a tube current time product may be used as in the table shown in FIG. 10.

As the lower limit of the tube current time product is set in the range of the first imaging condition by such a table, a second imaging condition having a too small cumulative dose of radiation is determined to be out of the first imaging condition range. Such a configuration can prevent the cumulative dose of radiation from being set too low.

A table in which a type of radiation irradiation apparatus 1 is linked with a irradiation time may be used as shown in FIG. 11. In this table, a lower limit of the irradiation time is linked with each apparatus type. In other words, the second imaging condition and the first imaging condition include a condition of the irradiation time in the preliminary exposure.

It is commonly known that an extremely short irradiation time by an apparatus results in an unstable radiation output. A too short irradiation time as the second imaging condition thus may cause the cumulative dose obtained from the preliminary exposure to become unstable, and thus the cumulative dose obtained from the main exposure may also become unstable.

Therefore, referring to the table, in which the lower limit of the irradiation time for each apparatus to be used is described, enables the reduction of the instability in the cumulative dose due to the irradiation time becoming too short, thereby stabilizing the cumulative dose. In addition, the first imaging condition that reflects the difference between the apparatuses to be used can be set.

Further, when the second imaging condition is the tube current time product, the tube current time product may be divided into the tube current and the irradiation time by console 3 or the like, and the obtained irradiation time may be adjusted so as not to become lower than the lower limit of the irradiation time in the table.

When taking images of areas where body movements are more likely to occur or of patients who are more likely to move their body (for example, children and elderly people), prioritizing shortening of the irradiation time over radiation stability may reduce the frequency of imaging failures as a result. In such cases, a table in which a imaging area, patient attributes and a lower limit of irradiation time are linked with each other may be used.

The longer the irradiation time, the greater the body movement of the patient (subject) that occurs between the beginning and the end of image capturing becomes. For the image capturing of areas where body movements are more likely to occur or of patients who are more likely to move their body (for example, children and elderly people), the upper limit of the irradiation time is set by using a table in which a imaging area, patient attributes and a upper limit of irradiation time are linked with each other. This configuration can reduce the frequency of imaging failures due to body movement.

The determination of the first irradiation condition that reflects such an influence of body movement is effective even in a configuration in which image combining processing is not performed on main-image data by using pre-image data, but this determination is particularly effective in the configuration in which the image combining processing is performed (step S108 shown in FIG. 8 above) because changes in the geometrical arrangement of the subject between the pre-image and the main-image can be reduced, enabling highly accurate image combining.

A table in which an imaging area, an imaging direction and an irradiation field in a radiation imaging system are linked with each other may be used as shown in FIG. 12. In the table, an imaging area, an imaging direction, and four distances as follows are linked with each other: a distance from the center of an irradiation surface of an imaging table to the upper boundary of an expected irradiation field as the upper boundary of the irradiation field, a distance from the center of the irradiation surface of the imaging table to the lower boundary of the expected irradiation field as the lower boundary of the irradiation field, a distance from the center of the irradiation surface of the imaging table to the left boundary of the expected irradiation field as the left boundary of the irradiation field, and a distance from the center of the irradiation surface of the imaging table to the right boundary of the expected irradiation field as the right boundary of the irradiation field. In other words, the second imaging condition and the first imaging condition include a condition relating to a geometrical arrangement of an irradiation field in a radiation imaging system.

When an irradiation field does not include the geometrical region to be used for obtaining a cumulative dose, the cumulative dose cannot be accurately calculated and thus the imaging condition in the main exposure becomes inappropriate.

For example, for a configuration in which a region of interest (ROI) is detected from pre-image data in the preliminary exposure to obtain a cumulative dose from pixel value information in the ROI, it is desirable that the ROI be housed within the irradiation field. Since ROIs are largely defined by the imaging area and the imaging direction, the irradiation field boundary where the assumed ROIs is housed can be linked with the imaging area and the imaging direction to be listed in the table.

Figure 13:
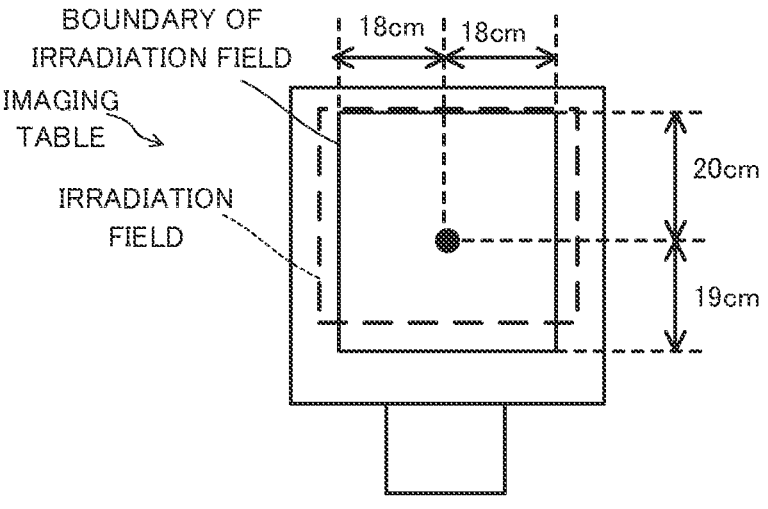
FIG. 13 illustrates an example in which an irradiation field boundary and an irradiation field are superimposed on an imaging table.

When, for example, the imaging area is chest and the imaging direction is front, control unit 31 acquires the information on the irradiation field boundary of No. 1 as the first imaging condition with referring to the table. In FIG. 13, the information on the irradiation field boundary of No. 1 is indicated by a solid line on an imaging table.

Control unit 31 acquires information on an irradiation range from, for example, a collimator provided in radiation irradiation apparatus 1, as a second imaging condition. Here is an obtained example having information of 19 cm in the upward direction, 19 cm in the downward direction, 20 cm in the left direction, and 20 cm in the right direction, from the center of the irradiation field.

Radiation irradiation apparatus 1 obtains the relative positions of the center of irradiation field and the center of the irradiation surface on an imaging table from the information on the focal position and orientation of a tube bulb and the center position of the irradiation surface on the imaging table, and outputs the relative positions to console 3. The information is of, for example, the center of irradiation field being shifted 1 cm in the upward direction from the center of the irradiation surface on the imaging table, and not shifted laterally.

When the information of the irradiation field range is the position of the broken line when the relative positions of the center of the irradiation field and the center of the irradiation surface on the imaging table are considered, the irradiation field boundary in the first imaging condition protrudes 1 cm downward from the irradiation field (broken line) in the second imaging condition described above. Control unit 31 thus determines that the second imaging condition falls out of the first imaging condition range.

When the second imaging condition is not within the first imaging condition, the collimator is set so that the irradiation field boundary is housed within the irradiation field or the irradiation field becomes larger than the irradiation field boundary. That is, control unit 31 controls the irradiation field based on the geometrical arrangement of the irradiation field. For a configuration in which a ROI is detected from pre-image data in a preliminary exposure and the cumulative dose is obtained from the pixel value information in the ROI, the burden on the user to understand the subject boundary for each imaging area is high because the irradiation field boundary where the assumed ROI is housed changes for each imaging area. Consequently, the user is more likely to set an inappropriate irradiation field. This configuration, on the other hand, greatly improves user-friendliness as control unit 31 controls the irradiation field.

Figure 14:
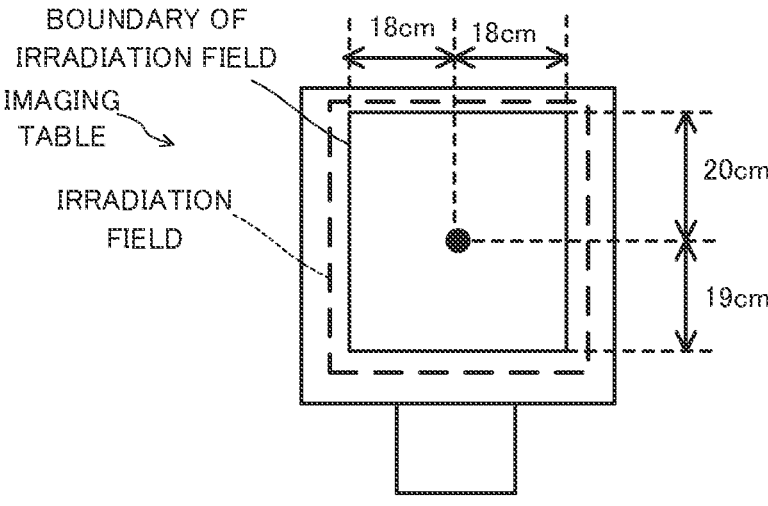
FIG. 14 illustrates an example in which an irradiation field boundary and an irradiation field are superimposed on the imaging table.

For example, an irradiation field (dashed line) is set so as to completely cover the irradiation field boundary (solid line) as shown in FIG. 14. Control unit 31 thus determines that the second imaging condition falls in the first imaging condition range.

By setting the confirmation timing of the irradiation field to be a timing, for example, after a certain period of time has passed since the irradiation field was changed, or after exposure switch 12 is pressed, console 3 can always acquire the latest irradiation field information. This configuration can reduce the frequency at which the second imaging condition is determined to be out of the first imaging condition range due to irradiation field change by the user.

Although the table shown in FIG. 12 did not refer to the body size of a user (patient), a plurality of tables relating to the boundaries of irradiation fields according to the body size of the patient may be prepared, and a suitable table may be selected according to the body size information of the patient.

Further, two or more of the above-described tables shown in FIGS. 4, 9, 10, 11 and 12 may be used in combination.

In addition to the imaging area and imaging direction, the following conditions may be linked with the first imaging condition: subject body pressure, subject body type, presence or absence of implants, distance from focal spot to image receiver, distance from focal spot to skin, intrinsic filtration value of radiation irradiation apparatus 1, presence or absence of additional filter, type of additional filter, presence or absence of scattered radiation removal grid, and type of scattered radiation removal grid and the like. A table may be obtained by combining all of these conditions, or an upper limit of the tube current time product may be set by selecting, for example, the minimum condition among all these conditions. This configuration improves the flexibility of the user's imaging condition selection.

These examinations condition may be acquired by any method other than input by the user. For example, for the distance from focal spot to image receiver and the distance from focal spot to skin, control unit 31 may acquire a distance obtained from the position information of the tube bulb and the imaging table on radiation irradiation apparatus 1 side, a distance measured by a range finder, a distance associated with the imaging table to be used for image capturing from the user-operation, and the like. A preset value, such as 180 cm in the case of a stereoscopic imaging table and 100 cm for a lying position imaging table, may be set in advance as the distance from focal spot to image receiver.

For the information on the additional filter and the information on the scattered radiation removal grid, information acquired by radiation irradiation apparatus 1 side may be used. In addition, information such as the subject body pressure, subject body type, and presence or absence of implants attached to patient information from RISs may be used. The subject body pressure and subject body type determined based on the patient age attached to the patient information may be used from the RISs.

The sensitivity may differ depending on the type of radiation imaging apparatus 2, or the dynamic range of the pixel value may differ. In addition, two types of detectors (for example, Gos and CsI) may be used in one radiation imaging apparatus 2. Since the difference between these apparatuses affects the upper limit of the tube current time product, different tables according to the type of apparatus may be used.

In the above embodiment, whether or not the second imaging condition is within the first imaging condition range is determined at the time of preliminary exposure, but the present invention is not limited thereto. For example, control unit 31 may determine whether the second imaging condition is within the both ranges of the third imaging condition in the preliminary exposure and the fourth imaging condition in the main exposure.

For example, for the second imaging condition in which the tube voltage and the tube current common in both the preliminary exposure and the main exposure are input, console 3 or the like determines the irradiation time for both the preliminary exposure and the main exposure. Console 3 then calculates the tube current time product (dose range per hour) based on the irradiation times and the input tube voltage and tube current to determine whether or not the obtained imaging condition is suitable for both the preliminary exposure and the main exposure.

The irradiation time of main exposure preferably be relatively short from the effect of the body movement of a subject. However, when the tube voltage and tube current in the second imaging condition are set to relatively small values, it is necessary to take a long irradiation time in the main exposure. Therefore, determining whether or not an irradiation time falls within the range of the optimum irradiation time in the main exposure (fourth imaging condition) based on the input tube voltage and tube current enables the irradiation time in main exposure to become an appropriate condition.

Control unit 31 may also notify the user of the range satisfying both the third imaging condition and the fourth imaging condition.

In the above embodiment, the second imaging condition is set by input from a user, but the present invention is not limited thereto. For example, when an imaging area and a imaging direction and the like are input, a tube voltage and a tube current time product associated with them may be automatically set as the second imaging condition, or the second imaging condition may be automatically set based on the examination order from the RIS.

In the above embodiment, control unit 31 allows any of a cumulative dose range in the preliminary exposure, an irradiation time in the preliminary exposure, and a geometrical arrangement of an irradiation field in the radiation imaging apparatus to be included in the first imaging condition, but the present invention is not limited thereto. For example, control unit 31 may allow two or more of the cumulative dose range, the irradiation time and the geometrical arrangement of the irradiation field to be included in the first imaging condition.

Further, the user inputs the second imaging condition again after the second imaging condition is determined not to be within the first imaging condition range in the above embodiment, but the present invention is not limited thereto. The apparatus may automatically input the second imaging condition again to fall within the first imaging condition range. In such cases, the user may be notified of the second imaging condition after the re-input. This configuration assist the user to set the second imaging condition to fall within the first imaging condition range.

In the above embodiment, the first imaging condition is acquired with reference to the table stored in storage unit 33, but the present invention is not limited thereto. A first imaging condition stored in an external storage apparatus may be acquired.

In the above embodiment, the imaging control apparatus is a console provided in a radiation imaging system, but the present invention is not limited thereto. For example, the imaging control apparatus may be an external apparatus provided in a place other than the radiation imaging system. In this case, for example, the imaging control apparatus outputs information based on the compatibility between the first imaging condition and the second imaging condition by radio communication or the like to the radiation imaging system.

In the above embodiment, the imaging control apparatus is configured separately from the radiation irradiation apparatus and the radiation imaging apparatus, but the present invention is not limited thereto. The imaging control apparatus may be incorporated in the radiation irradiation apparatus or the radiation imaging apparatus.

In the above embodiment, the control unit in the imaging control apparatus is configured integrally with the storage unit, the display unit, the operation unit and the like, but the present invention is not limited thereto. The control unit may be configured separately from the storage unit, the display unit, the operation unit and the like. In this case, the control unit may be provided, for example, in the radiation irradiation apparatus. When the control unit is provided in the radiation irradiation apparatus, input reception of an imaging condition is performed on the radiation irradiation apparatus side, and image processing is performed on a console side or the like depending on the radiation irradiation system.

The above embodiment has a configuration in which one main exposure is performed after one preliminary exposure, but the present invention is not limited thereto. A configuration in which a plurality of main exposures are performed after one preliminary exposure is also possible. In this configuration, control unit 31 performs an automatic exposure control to decide the imaging conditions for the plurality of main exposure based on a preliminary exposure image obtained in the preliminary exposure and the incidental information associated with the preliminary exposure image.

In addition, all of the above embodiments are merely illustrative of embodiments in practicing the present invention, and the technical scope of the present invention should not be construed as being limited thereto. In other words, the present invention may be further modified within the scope and spirit of the invention defined by the appended claims.

Although embodiments of the present invention have been described and illustrated in detail, the disclosed embodiments are made for purposes of illustration and example only and not limitation. The scope of the present invention should be interpreted by terms of the appended claims.

What is claimed is:

1. An imaging control apparatus, comprising:
   a hardware processor configured to acquire an imaging condition for a preliminary exposure that performs an exposure of radiation on a subject prior to a main exposure, wherein
   the hardware processor is configured to acquire an examination condition of the subject and adjust the acquired imaging condition based on the acquired examination condition,
   the acquired imaging condition for the preliminary exposure is a second imaging condition, and
   the hardware processor is further configured to acquire a first imaging condition based on the acquired examination condition, perform a comparison of the first imaging condition to the second imaging condition to determine whether or not the second imaging condition falls within a range of the first imaging condition, and adjust the second imaging condition so as to fall within the range of the first imaging condition when the comparison determines that the second imaging condition does not fall within the range of the first imaging condition.

2. The imaging control apparatus according to claim 1, wherein
   the hardware processor configured to acquire the second imaging condition based on a user input on an operation unit.

3. The imaging control apparatus according to claim 1, wherein
   the examination condition includes any one or more of a body size of a patient, an imaging area of the subject, an imaging direction, a subject body pressure, a subject body type, presence or absence of implants, a distance from focal spot to image receiver, a distance from focal spot to skin, an intrinsic filtration value of a radiation irradiation apparatus, presence or absence of additional filter, a type of additional filter, presence or absence of scattered radiation removal grid, a type of scattered radiation removal grid, a type of the radiation irradiation apparatus and a type of a radiation imaging apparatus.

4. The imaging control apparatus according to claim 3, wherein
   the examination condition is based on any of imaging order information from an external apparatus, patient information from the external apparatus, an input on an operation unit, patient information and patient age.

5. The imaging control apparatus according to claim 3, wherein any one or more examination conditions of the presence or absence of additional filter, the type of additional filter, the presence or absence of scattered radiation removal grid and the type of scattered radiation removal grid are acquired from the radiation irradiation apparatus.

6. The imaging control apparatus according to claim 3, wherein:

any one or more examination conditions of the distance from focal spot to image receiver and the distance from focal spot to skin are any of a distance obtained from position information of a tube bulb and an imaging table, a distance measured by a range finder and a distance associated with the imaging table to be used for image capturing from an input to an operation unit.

7. The imaging control apparatus according to claim 1, wherein:

the first imaging condition includes any one or more of a tube voltage, a tube current, an irradiation time and a tube current time product.

8. The imaging control apparatus according to claim 7, wherein:

a tube current time product of the second imaging condition is divided into the tube current and the irradiation time so as to fall within the range of the first imaging condition.

9. The imaging control apparatus according to claim 1, wherein:

the range of the first imaging condition is any of an upper limit, a lower limit and a combination of the upper limit and the lower limit.

10. The imaging control apparatus according to claim 1, wherein:

the range of the first imaging condition is related to a geometrical arrangement of an irradiation field in a radiation imaging system including the imaging control apparatus.

11. The imaging control apparatus according to claim 1, wherein:

the hardware processor is configured to notify a user of the adjusted second imaging condition.

12. A radiation imaging system, comprising:

a radiation irradiation apparatus that emits radiation for exposure; and the imaging control apparatus according to claim 1.

13. The imaging control apparatus according to claim 1, wherein the hardware processor is configured to acquire the second imaging condition based on a user input on an operation unit or an examination order, the second imaging condition specifies a condition selected from the group consisting of a specific tube voltage, a specific tube current, and a specific irradiation time and tube current time product, the examination condition is associated with a first imaging condition range, and the hardware processor is configured to adjust the second imaging condition to be within the first imaging condition range.

14. The imaging control apparatus according to claim 1, wherein:

the range of the first imaging condition is an imaging condition that enables appropriate imaging for the acquired examination condition.

15. A imaging control method, comprising:

acquiring a second imaging condition as an imaging condition for a preliminary exposure performed prior to a main exposure that performs an exposure of radiation on a subject;

acquiring an examination condition of the subject;

acquiring a first imaging condition based on the acquired examination condition;

comparing the first imaging condition to the second imaging condition to determine whether or not the second imaging condition falls within a range of the first imaging condition; and adjusting the second imaging condition so as to fall within a range of the first imaging condition when the step of comparing determines that the second imaging condition does not fall within the range of the first imaging condition.

* * * * *